US010327626B2

(12) United States Patent
Nishio (10) Patent No.: US 10,327,626 B2
(45) Date of Patent: Jun. 25, 2019

(54) LIGHT SOURCE APPARATUS FOR EMITTING LIGHT IN ACCORDANCE WITH ADJUSTED DRIVING CONDITION AND ENDOSCOPE APPARATUS

(71) Applicant: OLYMPUS CORPORATION, Tokyo (JP)

(72) Inventor: Masahiro Nishio, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 291 days.

(21) Appl. No.: 15/255,436

(22) Filed: Sep. 2, 2016

(65) Prior Publication Data

US 2016/0367124 A1   Dec. 22, 2016

Related U.S. Application Data

(63) Continuation of application No. PCT/JP2015/056382, filed on Mar. 4, 2015.

(30) Foreign Application Priority Data

Mar. 6, 2014   (JP) .................................. 2014-044170

(51) Int. Cl.
*A61B 1/06*   (2006.01)
*H01S 5/068*   (2006.01)
(Continued)

(52) U.S. Cl.
CPC ............ *A61B 1/063* (2013.01); *A61B 1/0638* (2013.01); *A61B 1/0661* (2013.01); *A61B 1/128* (2013.01);
(Continued)

(58) Field of Classification Search
CPC ......... A61B 1/063; A61B 1/0661; A61B 1/06; A61B 1/128; A61B 1/00006; H01S 5/06216; H01S 5/0617; G02B 23/2461
See application file for complete search history.

(56) References Cited

U.S. PATENT DOCUMENTS 5,835,250 A   11/1998   Kanesaka
5,987,044 A *   11/1999   Odagawa ............ H01S 5/06209
                                                               372/38.02
(Continued)

FOREIGN PATENT DOCUMENTS

JP   H01-232782 A   9/1989
JP   H01-303775 A   12/1989
(Continued)

OTHER PUBLICATIONS

Japanese Office Action dated Oct. 31, 2017 in Japanese Patent Application No. 2014-044170.
(Continued)

*Primary Examiner* — John P Leubecker
(74) *Attorney, Agent, or Firm* — Scully, Scott, Murphy & Presser, P.C.

(57) ABSTRACT

A light source apparatus includes at least one light-emitter, a driving circuit, an input unit, a temperature control circuit, and an effective light power setting circuit. The driving circuit allows the light-emitter to emit light by applying a driving waveform to the light-emitter. The effective light power setting circuit drives the driving circuit to allow the light-emitter to emit light with a predetermined effective light power, in accordance with a driving condition set by the temperature control circuit. The temperature control circuit controls the light-emitter to be in a predetermined heat generation state by increasing or decreasing a heat generation amount of the light-emitter without changing the
(Continued)

predetermined effective light power of the light emitted from the light-emitter by adjusting the driving condition of the light-emitter.

4 Claims, 10 Drawing Sheets (51) Int. Cl.
| | |
|---|---|
| A61B 1/12 | (2006.01) |
| H01S 5/40 | (2006.01) |
| H01S 5/024 | (2006.01) |
| H01S 5/042 | (2006.01) |
| H01S 5/00 | (2006.01) |
| A61B 1/00 | (2006.01) |
| A61B 1/04 | (2006.01) |
| H01S 5/062 | (2006.01) |
| H01S 5/06 | (2006.01) |

(52) U.S. Cl.
CPC .......... *H01S 5/02415* (2013.01); *H01S 5/042* (2013.01); *H01S 5/068* (2013.01); *H01S 5/06804* (2013.01); *H01S 5/4012* (2013.01); *H01S 5/4025* (2013.01); *A61B 1/00006* (2013.01); *A61B 1/04* (2013.01); *H01S 5/005* (2013.01); *H01S 5/02469* (2013.01); *H01S 5/0617* (2013.01); *H01S 5/06216* (2013.01)

(56) References Cited

U.S. PATENT DOCUMENTS

| | | | | |
|---|---|---|---|---|
| 6,795,656 | B1 * | 9/2004 | Ikeuchi | ............... H01S 5/042 372/29.014 |
| 7,054,343 | B1 * | 5/2006 | Wu | ................. H01S 5/0014 372/32 |
| 2004/0240495 | A1 | 12/2004 | Akamatsu | |
| 2006/0022214 | A1 * | 2/2006 | Morgan | .................. F21K 9/00 257/99 |
| 2007/0030176 | A1 * | 2/2007 | Sanchez-Olea | ....... H01S 5/0014 341/13 |
| 2007/0112247 | A1 * | 5/2007 | Hirata | .................. A61B 1/0607 600/101 |
| 2008/0165810 | A1 | 7/2008 | Takeda | |
| 2010/0098119 | A1 | 4/2010 | Schemmann et al. | |
| 2010/0228089 | A1 * | 9/2010 | Hoffman | ................ A61B 1/063 600/182 |
| 2012/0236888 | A1 * | 9/2012 | Tang | ..................... H01S 5/0683 372/38.02 |
| 2012/0281390 | A1 * | 11/2012 | Nakamura | ............. A61B 90/35 362/103 |
| 2012/0327964 | A1 * | 12/2012 | Ichino | ................ H01S 5/06804 372/29.015 |
| 2013/0193875 | A1 * | 8/2013 | Godo | .................. A61B 1/0684 315/297 |
| 2014/0307071 | A1 * | 10/2014 | Hirosawa | ........... A61B 1/00133 348/65 |

FOREIGN PATENT DOCUMENTS

| | | | | |
|---|---|---|---|---|
| JP | H05-041558 | A | | 2/1993 |
| JP | 05075192 | A | * 3/1993 | ............. G11B 7/126 |
| JP | H09-064441 | A | | 3/1997 |
| JP | 2002-270950 | A | | 9/2002 |
| JP | 2004-356579 | A | | 12/2004 |
| JP | 2007-043068 | A | | 2/2007 |
| JP | 2009-152516 | A | | 7/2009 |
| JP | 2010-506394 | A | | 2/2010 |

OTHER PUBLICATIONS

English translation of International Preliminary Report on Patentability dated Sep. 15, 2016 together with the Written Opinion received in related International Application No. PCT/JP2015/056382.

International Search Report dated Jun. 2, 2015 issued in corresponding International Patent Application No. PCT/JP2015/056382.

* cited by examiner

LIGHT SOURCE APPARATUS FOR EMITTING LIGHT IN ACCORDANCE WITH ADJUSTED DRIVING CONDITION AND ENDOSCOPE APPARATUS

CROSS-REFERENCE TO RELATED APPLICATIONS

This application is a Continuation Application of PCT Application No. PCT/JP2015/056382, filed Mar. 4, 2015 and based upon and claiming the benefit of priority from the prior Japanese Patent Application No. 2014-044170, filed Mar. 6, 2014, the entire contents of which are incorporated herein by reference.

BACKGROUND OF THE INVENTION

1. Field of the Invention

The present invention relates to a light source apparatus for converting laser light emitted from a semiconductor laser (hereinafter referred to as "LD"), for example, to illumination light used for monitoring and outputting the illumination light. Furthermore, the present invention relates to an endoscope apparatus including the light source apparatus, and to a light source control method for controlling the light source apparatus.

2. Description of the Related Art

For example, US Publication No. 2004/0240495 discloses a technique of converting laser light emitted from an LD to illumination light. A laser light output apparatus disclosed in the US Publication includes a plurality of LDs as light sources. For each LD, the apparatus includes a temperature adjustment mechanism formed of a temperature adjuster (Peltier device) and a driving circuit that drives the element.

BRIEF SUMMARY OF THE INVENTION

According to a first aspect of the invention there is provided a light source apparatus including at least one light-emitter configured to emit light, a driving circuit configured to apply a driving waveform to the light-emitter, an input unit configured to input a predetermined effective light power of the light emitted from the light-emitter, a temperature control circuit configured to control the light-emitter to be in a predetermined heat generation state by increasing or decreasing a heat generation amount of the light-emitter without changing the predetermined effective light power of the light emitted from the light-emitter by adjusting a driving condition of the light-emitter, and an effective light power setting circuit configured to drive the driving circuit to allow the light-emitter to emit light with the predetermined effective light power, in accordance with the driving condition adjusted by the temperature control circuit.

According to a second aspect of the invention there is provided an endoscope apparatus including the light source apparatus according to the first aspect of the present invention, and an image sensor configured to image a subject illuminated by light from the light source apparatus.

According to a third aspect of the invention there is provided a light source control method including inputting a predetermined effective light power of light emitted from at least one light-emitter, setting a driving condition of the at least one light-emitter, driving a driving circuit which applies a driving waveform to the light-emitter so as to emit light with the predetermined effective light power, in accordance with the driving condition, and controlling the light-emitter to be in a predetermined heat generation state by increasing or decreasing a heat generation amount of the light-emitter without changing the predetermined effective light power of the light emitted from the light-emitter by adjusting the driving condition of the light-emitter.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

The first embodiment of the present invention will be described with reference to the drawings.

Figure 1:
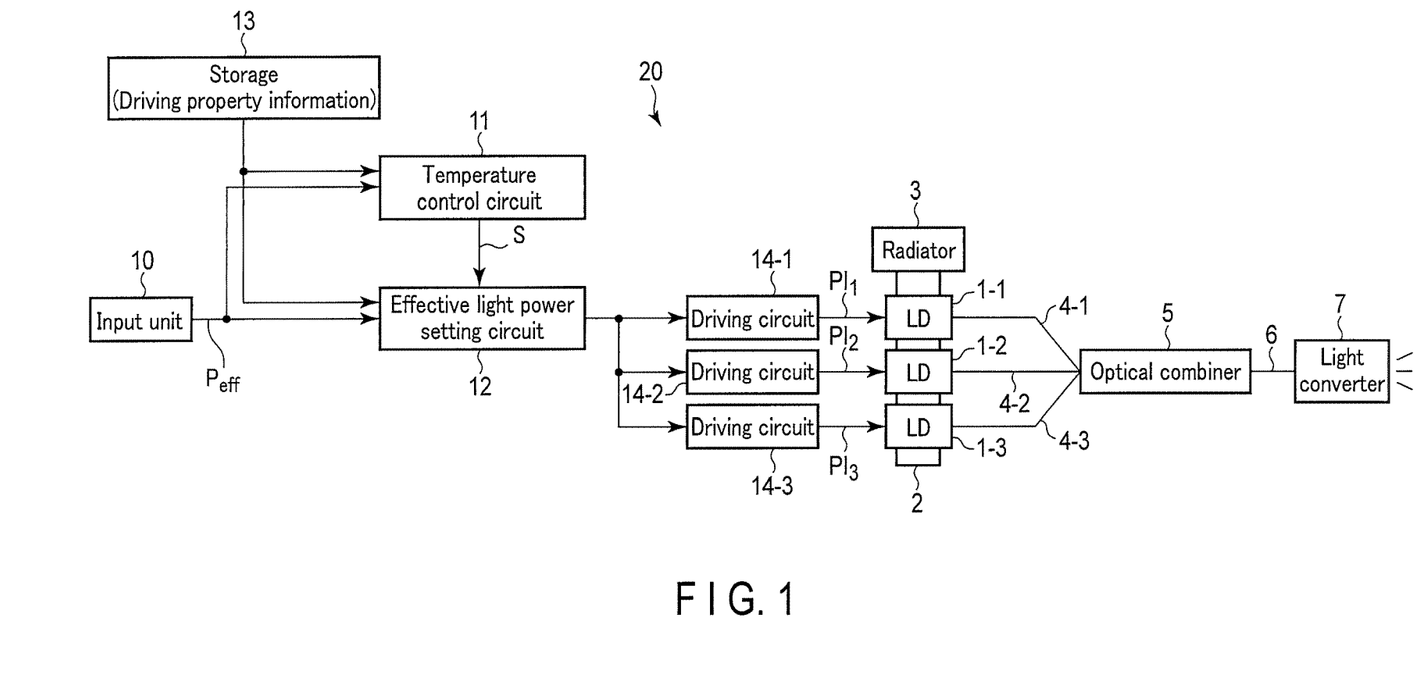
FIG. 1 is a block diagram illustrating a first embodiment of a light source apparatus according to the present invention.
Figure 2:
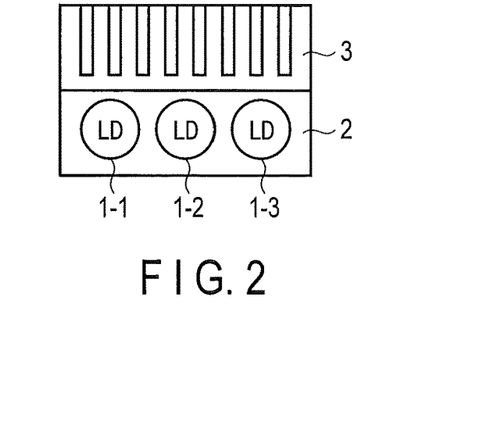
FIG. 2 illustrates a configuration of a peripheral portion of LDs.

As shown in FIG. 1, a light source apparatus 20 includes a plurality of semiconductor lasers (LDs) which are light-emitters, for example, LD 1-1 to LD 1-3. As shown in FIG. 2, each of LD 1-1 to LD 1-3 is fixed on a mount 2. Each of LD 1-1 to LD 1-3 emits laser light when a current having a cyclic pulse waveform as a driving waveform is applied. The number of semiconductor lasers (LDs) is not limited to three, but may be two or four or more.

[Thermal Connection Relationship]

Each of LD 1-1 to LD 1-3 generates heat when emitting laser light. The mount 2 and each of LD 1-1 to LD 1-3 are thermally connected to each other. The mount 2 is provided with a radiator 3. The radiator 3 discharges heat generated by each of LD 1-1 to LD 1-3 outside of the light source apparatus 20 (into the atmosphere, for example).

[Optical Connection Relationship]

An output terminal of each of LD 1-1 to LD 1-3 is optically connected to an optical combiner 5 through respective optical fibers 4-1 to 4-3. An optical lens (not shown) is arranged between the output terminal of each of LD 1-1 to LD 1-3 and the respective optical fibers 4-1 to 4-3. The output terminal of each of LD 1-1 to LD 1-3 is optically connected to the respective optical fibers 4-1 to 4-3 by the optical lens.

An output terminal of the optical combiner 5 is optically connected to a light converter 7 through an optical fiber 6. The optical combiner 5 combines laser light guided by each of the optical fibers 4-1 to 4-3, and outputs the combined laser light to the light converter 7 through the optical fiber 6.

The light converter 7 includes, for example, a phosphor. When laser light from the optical fiber 6 enters the light converter 7, the laser light is applied to the phosphor. When the laser light is applied, the phosphor generates fluorescence by the applied laser light and allows part of the laser light to pass through. The light converter 7 accordingly generates illumination light L generated by mixing the fluorescent and the laser light that has passed through the phosphor.

[Electrical Connection Relationship]

The light source apparatus 20 is provided with an input unit 10 and a storage 13. The input unit 10 and the storage 13 both are connected to a temperature control circuit 11 and an effective light power setting circuit 12.

The input unit 10 includes a user-interface such as a keyboard, switches and dials which input an output command value of each of LD 1-1 to LD 1-3, i.e., a predetermined effective light power $P_{eff}$ of laser light respectively set relative to each of LD 1-1 to LD 1-3, upon reception of a manual operation by an operator, for example. The input unit 10 may include a receiver which receives the output command value wireless- or wired-transmitted from an external transmitter. The apparatus 20 includes, for example, three of LD 1-1 to LD 1-3, and accordingly the predetermined effective light power $P_{eff}$ for each of LD 1-1 to LD 1-3 is input to the input unit 10. For example, an effective light power $P_{eff1}$ for LD 1-1, an effective light power $P_{eff2}$ for LD 1-2, and an effective light power $P_{eff3}$ for LD 1-3 are input to the input unit 10. The predetermined effective light powers $P_{eff1}$, $P_{eff2}$ and $P_{eff3}$ for LD 1-1 to LD 1-3 input to the input unit 10 are transmitted to the temperature control circuit 11 and the effective light power setting circuit 12.

The storage 13 stores driving property information for each of LD 1-1 to LD 1-3. The driving property information is obtained by measuring the properties of each of LD 1-1 to LD 1-3 before using the light source apparatus 20, for example, at the time of shipment from a factory. The storage 13 stores a threshold current $I_{th}$ (described later), a forward voltage $V_f$, a slope efficiency η, and a maximum rated value $P_{max}$ of an output light power for each of LD 1-1 to LD 1-3, as respective driving property information. The storage 13 is formed, for example, of a nonvolatile memory.

The temperature control circuit 11 sets a driving condition S for each of LD 1-1 to LD 1-3. If the driving waveform for driving each of LD 1-1 to LD 1-3 is a cyclic pulse waveform, the driving condition S for each of LD 1-1 to LD 1-3 is one of a peak current value of the cyclic pulse waveform and a duty cycle. The temperature control circuit 11 transmits the peak current value or the duty cycle set as the driving condition S to the effective light power setting circuit 12.

The temperature control circuit 11 derives the peak current value of the cyclic pulse waveform or the duty cycle set as the driving condition S, based on the driving property information stored in the storage 13.

The temperature control circuit 11 adjusts the peak current value of the cyclic pulse waveform or the duty cycle set as the driving condition S to increase or decrease the amount of heat generation of each of LD 1-1 to LD 1-3 while not changing the effective light power $P_{eff}$ of laser light from each of LD 1-1 to LD 1-3, so that each of LD 1-1 to LD 1-3 is controlled to have respective predetermined heat generation conditions. The predetermined heat generation conditions are set so that the amount of heat generation of each of LD 1-1 to LD 1-3 becomes equal. That is, the temperature control circuit 11 adjusts the peak current value of the cyclic pulse waveform or the duty cycle set as the driving condition S of each of LD 1-1 to LD 1-3 so that the amount of heat generation of each of LD 1-1 to LD 1-3 becomes equal.

The effective light power setting circuit 12 drives each of driving circuits 14-1 to 14-3 so that each of LD 1-1 to LD 1-3 emits light with the predetermined effective light power $P_{eff}$ of laser light input from the input unit 10, in accordance with the driving condition S (the peak current value of the cyclic pulse waveform or the duty cycle) set by the temperature control circuit 11.

The effective light power setting circuit 12 may vary the cycle while setting the pulse width of the pulse waveform to be fixed, instead of using a pulse width modulation (PWM) to vary the duty cycle of the pulse waveform set as the driving condition S.

The effective light power setting circuit 12 determines the other of the peak current value of the cyclic pulse waveform and the duty cycle which has not been set as the driving condition S, so that the effective light power of laser light emitted from each of LD 1-1 to LD 1-3 becomes the predetermined effective light power $P_{eff}$.

The effective light power setting circuit 12 drives each of the driving circuits 14-1 to 14-3 with a continuous driving waveform so that each of LD 1-1 to LD 1-3 emits light in accordance with the predetermined effective light power $P_{eff}$ input from the input unit 10. The effective light power setting circuit 12 derives, from the respective driving property information of each of LD 1-1 to LD 1-3, a predicted heat generation amount when each of LD 1-1 to LD 1-3 emits light by driving each of the driving circuits 14-1 to 14-3.

One of LD 1-1 to LD 1-3 having the greatest predicted heat generation amount is set as a first light-emitter. LDs not set as the first light-emitter are set to be second light-emitters. By this processing, the temperature control circuit 11 sets the driving condition S of the first light-emitter for the highest light-emitting efficiency of the first light-emitter.

The output terminal of each of the driving circuits 14-1 to 14-3 is connected to the corresponding LD 1-1 to LD 1-3. Each of the driving circuits 14-1 to 14-3 drives each of LD 1-1 to LD 1-3 by applying the driving waveform to allow LD 1-1 to LD 1-3 to emit laser light.

Figure 3:
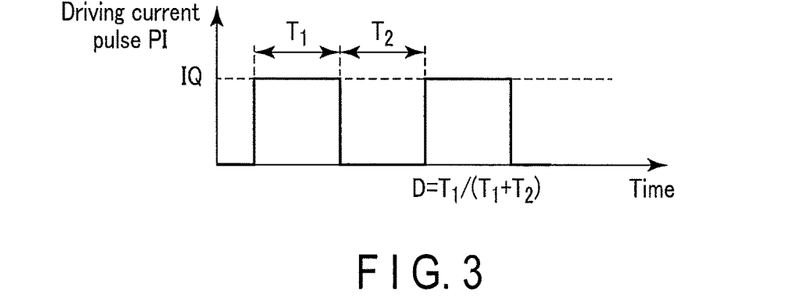
FIG. 3 illustrates a waveform of a driving current pulse to be applied to a LD.

Each of the driving circuits 14-1 to 14-3 applies a driving current pulse PI ($PI_1$ to $PI_3$) having a cyclic pulse waveform as shown in FIG. 3 to each of LD 1-1 to LD 1-3, in accordance with the peak current value and the duty cycle set by the effective light power setting circuit 12.

If it is assumed that a period for which each of the driving current pulses $PI_1$ to $PI_3$ is applied is $T_1$, and a period for which no driving current pulse is applied is $T_2$, the duty cycle D is given as follows:

$$D = T_1/(T_1+T_2) \quad (1).$$

A current applied during the period $T_1$ is referred to as a peak current IQ. The "$(T_1+T_2)$" represents a cycle of each of the driving current pulses $PI_1$ to $PI_3$.

The cycle $(T_1+T_2)$ of each of the driving current pulses $PI_1$ to $PI_3$ is set to a cycle in which each of LD 1-1 to LD 1-3 does not thermally respond. That is, The cycle $(T_1+T_2)$ is set to a cycle in which the temperature of each of LD 1-1 to LD 1-3 cannot respond to each pulse of the pulse driving, or each of LD 1-1 to LD 1-3 cannot response thermally. Alternatively, the cycle $(T_1+T_2)$ is set to a cycle in which the amount of change in temperature of each of LD 1-1 to LD 1-3 responding to each of the driving current pulses $PI_1$ to $PI_3$ does not make any effect.

[Properties and Heat Generation Amount when Pulse Driving LD 1-1 to LD 1-3]

The following explanation is based on values at points in time, not on an integrated value such as an effective light power $P_{eff}$.

The properties of LD 1-1 to LD 1-3 will be explained. LD 1-1 to LD 1-3 have the same properties. The heat generation amount Q of one LD is given as follows, where a power to be applied to the LD is $P_{in}$, a light output of the LD is $P_{out}$, a forward voltage of the LD is $V_f$, and driving current pulse PI of the LD is $I_{drv}$:

$$Q = P_{in} - P_{out} \quad (2)$$
$$= V_f \cdot I_{drv} - P_{out}.$$

Figure 4:
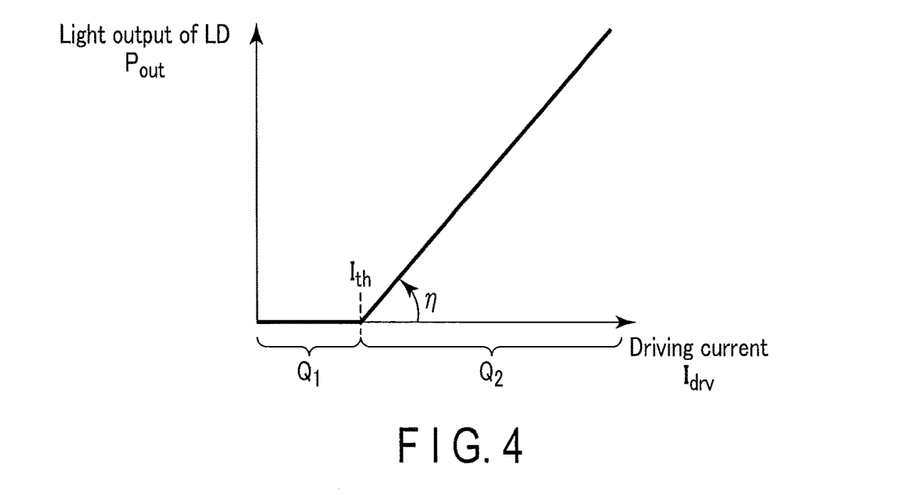
FIG. 4 illustrates a relationship between a driving current and a light output of a LD.

The LD does not emit laser light until the driving current pulse PI reaches a threshold current $I_{th}$, but emits laser light if the driving current pulse exceeds the threshold current $I_{th}$. The power of laser light output from the LD has properties of increasing essentially proportional to the amount of current that exceeds the threshold current $I_{th}$, as shown in FIG. 4.

The light emission efficiency of the LD has different properties depending on driving current pulse PI and the light output $P_{out}$ of the LD.

The relationships between the light output $P_{out}$, slope efficiency $\eta$, each of the driving current pulse PI ($I_{drv}$), and threshold current $I_{th}$ of the driving current pulse PI for the LD are represented by the following:

$$P_{out} = \eta \times (I_{drv} - I_{th}) \quad (3).$$

Accordingly, as is shown in FIG. 4, the heat generation amount of the LD is a total value ($Q_{all}=Q_1+Q_2$) of the heat generation amount $Q_1$ determined by the driving current pulse PI that does not reach the threshold current $I_{th}$, and the heat generation amount $Q_2$ determined by the driving current pulse PI that exceeds the threshold current $I_{th}$.

The following relationships are determined:

$$Q_1 = I_{th} \times V_f \quad (4)$$
$$Q_2 = (I_{drv} - I_{th}) \times V_f - P_{out}$$
$$= P_{out}(V_f/\eta - 1)$$
$$= P_{out} \times K.$$

$Q_1$ is fixed regardless of the light output $P_{out}$ of the LD, and $Q_2$ is proportional to the light power of the light output $P_{out}$.

Next, the effective light power $P_{eff}$ is explained based on the properties of LD 1-1 to LD 1-3.

As explained above, when each of the LD 1-1 to LD 1-3 is driven by the waveform of a pulse-like driving current such as driving current pulses $PI_1$ to $PI_3$, the laser light emitted from each of LD 1-1 to LD 1-3 is output as pulse-like light in accordance with each of the driving current pulses $PI_1$ to $PI_3$.

The effective light power $P_{eff}$ corresponds to the value obtained by integrating the light power by a sufficiently longer period than the cycle of pulse driving, when performing the pulse driving as shown in FIG. 3. For example, pulse-like light cannot be distinguished with the naked eyes or an image sensor, and light corresponding to the effective light power $P_{eff}$ obtained by integrating the pulse-like light is noticed.

The effective light power $P_{eff}$ is given by:

$$P_{eff} = D \times P_{out} \quad (5).$$

The light output $P_{out}$ of each of LD 1-1 to LD 1-3 corresponds to a peak light power $P_{out}$ of pulse-like light output, i.e., peak output.

On the other hand, an effective heat generation amount $Q_{eff}$ based on the heat generation amount Q is given by:

$$Q_{eff} = D \times D_{all} \quad (6)$$
$$= D \times (Q_1 + Q_2)$$
$$= D \times Q_1 + D \times P_{out} \times K$$
$$= D \times Q_1 + P_{eff} \times K.$$

In the effective heat generation amount $Q_{eff}$ represented by equation (6), the second term "$P_{eff} \times K$" does not change to obtain a desired effective light power $P_{eff}$, whereas the first term "$D \times Q_1$" can vary by changing the duty cycle D and the peak power $P_{out}$ of pulse-like light output.

Since the upper limit of the light output $P_{out}$ is the maximum rated value $P_{max}$ of the output light power of each of LD 1-1 to LD 1-3, the range of the duty cycle D is limited:

$$(P_{eff}/P_{max}) \leq D \leq 1 \quad (7).$$

If the duty cycle varies within the above range, the adjustable range of the effective heat generation amount $Q_{eff}$ is given by:

$$(P_{eff}/P_{max}) \times Q_1 + (P_{eff} \times K) \leq Q_{eff} \leq Q_1 + P_{eff} \times K \quad (8).$$

Figure 5A:
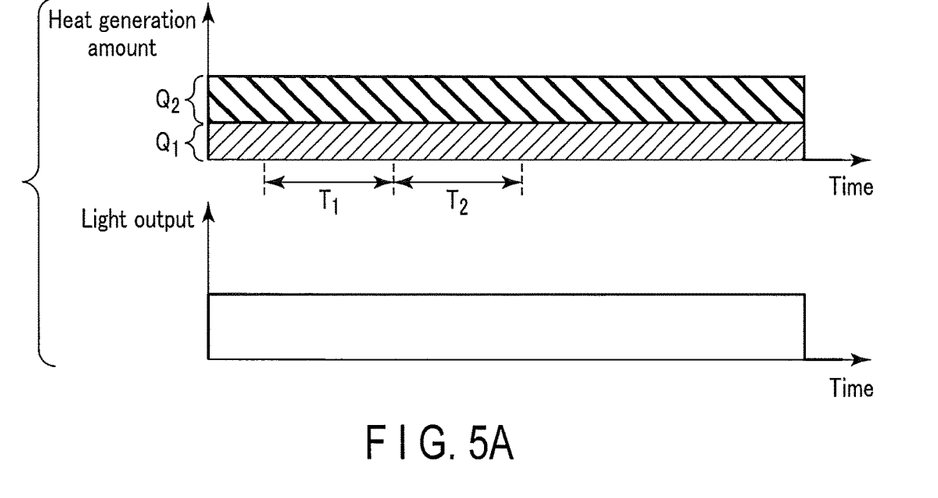
FIG. 5A illustrates a relationship between a heat generation amount and a light output when a duty cycle is 100%.
Figure 5B:
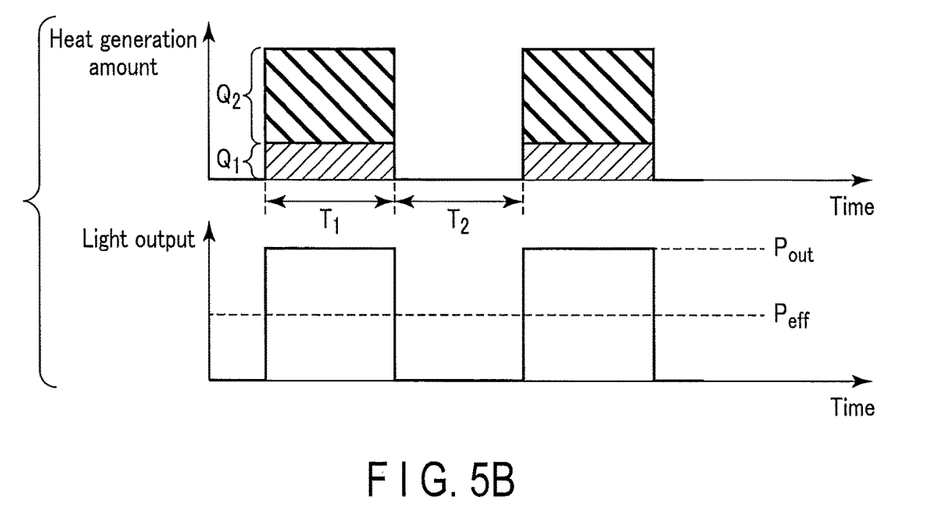
FIG. 5B illustrates a relationship between the heat generation amount and the light output when the duty cycle is 50% and an effective light power $P_{eff}$ is same in the 100% duty cycle.

FIGS. 5A and 5B illustrate the relationship between the heat generation amount and the light output when the effective light power $P_{eff}$ is the same. FIG. 5A illustrates the relationship between the heat generation amount and the light output when the duty cycle is 100%, and FIG. 5B illustrates the relationship between the heat generation amount and the light output when the duty cycle is 50%.

As shown in FIGS. 5A and 5B, the temporal mean of the heat generation amount $Q_2$ determined based on the driving current pulse PI that exceeds the threshold current $I_{th}$ with the duty cycle of 100%, and the temporal mean of the heat generation amount $Q_2$ with the duty cycle of 50%, are equal to each other.

On the other hand, the heat generation amount $Q_1$ determined based on the driving current pulse PI that does not reach the threshold current $I_{th}$ with the duty cycle of 50% is half of the heat generation amount $Q_1$ with the duty cycle of 100%.

Next, the operation of the light source apparatus 20 having the aforementioned configuration will be explained.

The effective light power $P_{eff1}$ for LD 1-1, the effective light power $P_{eff2}$ for LD 1-2, and the effective light power $P_{eff3}$ for LD 1-3 are input from the input unit 10. The effective light powers $P_{eff1}$, $P_{eff2}$, and $P_{eff3}$ are transmitted to the temperature control circuit 11 and the effective light power setting circuit 12. The relationships between the effective light powers $P_{eff1}$, $P_{eff2}$ and $P_{eff3}$ are, for example, $P_{eff1} < P_{eff2} < P_{eff3}$, and the effective light power $P_{eff3}$ for LD 1-3 is the highest.

The temperature control circuit 11 reads the driving property information for each of LD 1-1 to LD 1-3 stored in the storage 13, determines the driving condition S of each of LD 1-1 to LD 1-3, i.e., the peak current values (value of peak current IQ), of each of LD 1-1 to LD 1-3, based on the respective driving property information, and transmits the peak current values to the effective light power setting circuit 12.

The effective light power setting circuit 12 obtains each duty cycle D based on each of the peak current values input from the temperature control circuit 11, and transmits the peak current value and the duty cycle D to each of the driving circuits 14-1 to 14-3 connected to the respective LD 1-1 to LD 1-3.

Specifically, the temperature control circuit 11 first specifies an LD having the greatest heat generation amount (the first light-emitter) among LD 1-1 to LD 1-3.

That is, the temperature control circuit 11 reads the threshold current $I_{th}$, the forward voltage $V_f$, and the slope efficiency η for each of LD 1-1 to LD 1-3 from the respective driving property information stored in the storage 13. The temperature control circuit 11 obtains the heat generation amount $Q_2$ for each of LD 1-1 to LD 1-3 with the continuous waveform (duty cycle of 100%) as shown in FIG. 5A, by equation (2) using the threshold current $I_{th}$, the forward voltage $V_f$, and the slope efficiency η. The temperature control circuit 11 uses the continuous waveform (duty cycle of 100%) as shown in FIG. 5A, instead of a pulse waveform. In the present embodiment, since LD 1-1 to LD 1-3 have essentially the same properties, the heat generation amount Q of LD 1-3 whose effective light power $P_{eff}$ is highest is defined as the highest.

Next, the duty cycle D of pulse driving for LD 1-3 whose effective light power $P_{eff3}$ is greatest is determined to achieve high efficiency in order to further reduce heat generation. That is, the temperature control circuit 11 derives a peak current value of the cyclic pulse waveform or a duty cycle of LD 1-3 having the highest effective light power $P_{eff3}$, based on the driving property information stored in the storage 13, i.e., the threshold current $I_{th}$, the forward voltage $V_f$ of LD 1-3 and the slope efficiency η, and the maximum rated value $P_{max}$ of the output light power for LD 1-3.

The temperature control circuit 11 adjusts the peak current value of the cyclic pulse waveform or the duty cycle set as the driving condition S to increase or decrease the amount of heat generation of each of LD 1-1 to LD 1-3 while not changing the effective light power of laser light from each of LD 1-1 to LD 1-3, so that each of LD 1-1 to LD 1-3 is controlled to have respective predetermined heat generation conditions, i.e., respective heat generation amounts is equal to each other.

According to the embodiment, the light emission efficiency becomes greatest at the maximum rated value $P_{max}$ of the output light power of each of LD 1-1 to LD 1-3. Accordingly, the temperature control circuit 11 reads the maximum rated value $P_{max}$ of the output light power of LD 1-3 from the respective driving property information stored in the storage 13. The temperature control circuit 11 derives a current value or a duty cycle at which the output light power of LD 1-3 becomes the maximum rated value $P_{max}$, and outputs the current value or the duty cycle as a driving condition S to the effective light power setting circuit 12.

The effective light power setting circuit 12 drives the driving circuit 14-3 so that LD 1-3 emits light at a predetermined effective light power $P_{eff3}$ of laser light input from the input unit 10, in accordance with the driving condition S (the peak current value or the duty cycle) set by the temperature control circuit 11.

Specifically, the effective light power setting circuit 12 sets, for the driving circuit 14-3, the duty cycle $D_3$ of LD 1-3 so that the effective light power of LD 1-3 that has been defined as having the highest heat generation amount Q becomes $P_{eff3}$ if the input driving condition S is the peak current value. The duty cycle $D_3$ of this case is given by:

$$D_3 = P_{eff}/P_{max} \qquad (9).$$

In this case, the effective heat generation amount $Q_{eff3}$ of LD 1-3 is given by:

$$Q_{eff3} = D_3 \times Q_1 + D_3 \times P_{max} \times K. \qquad (10).$$

Next, the peak current value and the duty cycle D for the remaining LD 1-1 and LD 1-2 (the second light-emitters) are set in the same operation so that the heat generation amount of each of LD 1-1 and LD 1-2 is the same as that of LD 1-3.

For example, the effective heat generation amount $Q_{eff1}$ of LD 1-1 is given by:

$$Q_{eff1} = D_1 \times (Q_1 + P_1 \times K) \qquad (11),$$

where $P_1$ represents a peak output of LD 1-1.

The effective heat generation amount $Q_{eff1}$ of LD 1-1 is set to be the same as the effective heat generation amount $Q_{eff3}$ of LD 1-3. By using equation (6), the following conditions are true:

$$Q_{eff1} = D_1 \times Q_1 + P_{eff1} \times K$$

$$Q_{eff3} = D_3 \times Q_1 + P_{eff3} \times K.$$

Since $Q_{eff1} = Q_{eff3}$, $$D_1 \times Q_1 + P_{eff1} \times K = D_3 \times Q_1 + P_{eff3} \times K.$$

Accordingly, the duty cycle $D_1$ of LD 1-1 is set to be:

$$D_1 = D_3 + K/Q_1 \times (P_{eff3} - P_{eff1}).$$

The duty cycle $D_1$ of LD 1-1 is a state in which increases the duty cycle from the duty cycle $D_3$ of LD 1-3.

The relationship as represented by equation (11) is satisfied:

$$P_1 = \frac{Q_1}{k}\left(\frac{D_3}{D_1} - 1\right) + \frac{P_{eff3}}{D_1}.$$

Since the peak current value and the duty cycle D is set so that the effective heat generation amounts $Q_{eff1}$ and $Q_{eff2}$ of the remaining LD 1-1 and LD 1-2 are equal to the effective heat generation amount $Q_{eff3}$ of LD 1-3, the effective heat generation amounts $Q_{eff1}$, $Q_{eff2}$ and $Q_{eff3}$ of LD 1-1, LD 1-2, and LD 1-3 can be equal to each other.

By this processing, the effective light power setting circuit 12 drives each of the driving circuits 14-1 to 14-3 so that each of LD 1-1 to LD 1-3 emits light at a predetermined effective light power $P_{eff}$ of laser light input from the input unit 10, in accordance with the driving condition S (the peak current value or the duty cycle) set by the temperature control circuit 11.

According to the first embodiment, the temperature control circuit 11 derives the peak current value of the cyclic pulse waveform or the duty cycle set as the driving condition S, based on the driving property information stored in the storage 13. The temperature control circuit 11 also adjusts the peak current value of the cyclic pulse waveform or the duty cycle set as the driving condition S to increase or decrease the heat generation amount of each of LD 1-1 to LD 1-3, while not changing the effective light power of laser light from each of LD 1-1 to LD 1-3, so that each of LD 1-1 to LD 1-3 is controlled to have respective predetermined heat generation conditions. Then, the effective light power setting circuit 12 drives each of LD 1-1 to LD 1-3 in accordance with the peak current value or the duty cycle set as the driving condition S at the temperature control circuit 11. By this processing, the heat generation amount of each of LD 1-1 to LD 1-3 becomes equal even if different light output powers are set to LD 1-1 to LD 1-3. Accordingly, there is no need to specially provide an element to control the temperature, for example, a Peltier device. The first embodiment realizes, with a simple structure, equally controlling the temperature of LD 1-1 to LD 1-3, and improves output stability, but without lowering the performance.

If the duty cycle D of the second light-emitters (other than the first light-emitter (LD) having the greatest heat generation amount) exceeds 100%, there may be a case where the heat generation amounts of LD 1-1 to LD 1-3 cannot be equal even if the duty cycle D increases. Even in such a case, by increasing the light output $P_{out}$ (peak output) of the illumination light L with the duty cycle D of 100%, the effective light power $P_{eff}$ can be ensured, and the heat generation amounts of LD 1-1 to LD 1-3 can be set as close as possible.

The driving condition S, i.e., the duty cycle, or the peak current of the driving pulse waveform, may be always calculated and set based on the effective light power $P_{eff}$ to be input from the input unit 10, or may be calculated and set when the effective light power $P_{eff}$ input from the input unit 10 changes.

In addition, LD 1-1 to LD 1-3 may be arranged so that the heat conductance between the temperature adjuster and each of LD 1-1 to LD 1-3 becomes equal. That is, in the aforementioned embodiment, the heat generation amounts of LD 1-1 to LD 1-3 are set to be equal to each other; however, LD 1-1 to LD 1-3 may be arranged so that the heat conductance is equal between respective LD 1-1 to LD 1-3 and an atmosphere to which the heat is radiated, or that the heat conductance between the radiator 3 and each of LD 1-1 to LD 1-3 becomes equal.

If the heat conductance is different between respective LD 1-1 to LD 1-3 and the atmosphere to which heat is radiated, or the heat conductance between the radiator 3 and each of LD 1-1 to LD 1-3 becomes different to each other, each of the values may be obtained from the set value of the actually measured value, and the heat generation amount of each of LD 1-1 to LD 1-3 may be set to be inversely proportional to the value.

Figure 6:
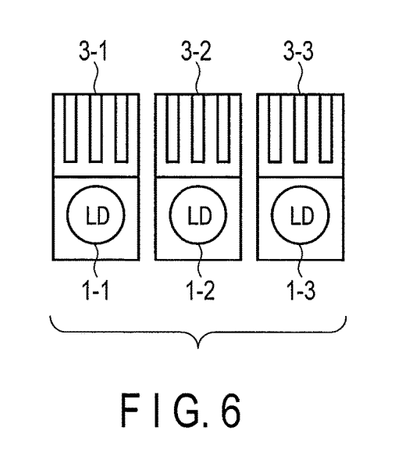
FIG. 6 illustrates another example of the configuration of the peripheral portion of LDs.

In the present embodiment, one radiator 3 is connected to LD 1-1 to LD 1-3; however, individual radiators 3-1 to 3-3 may be connected to each of LD 1-1 to LD 1-3, as shown in FIG. 6.

Second Embodiment

Figure 7:
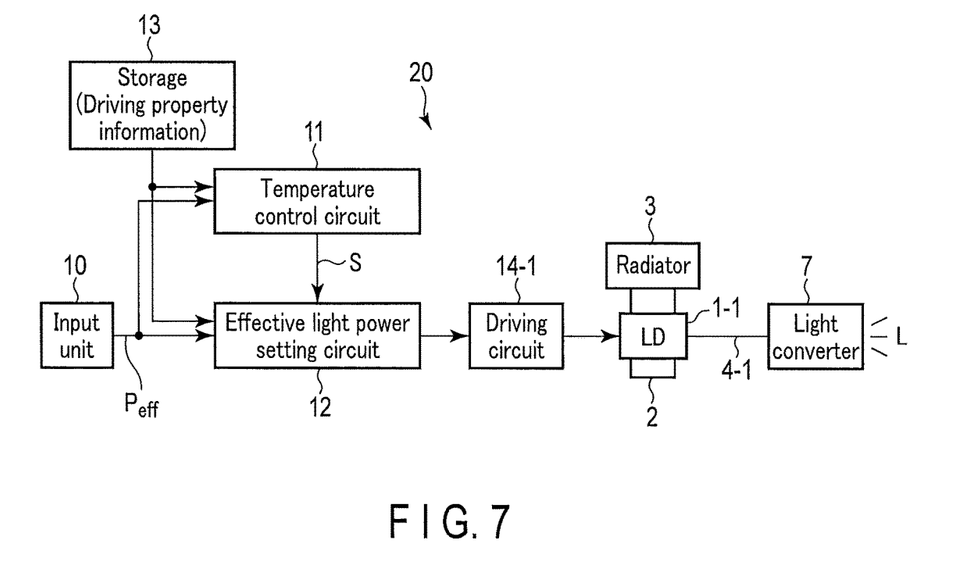
FIG. 7 is a block diagram illustrating a second embodiment of the light source apparatus according to the present invention.

FIG. 7 illustrates a configuration of the light source apparatus 20 according to a second embodiment. The same elements as those shown in FIG. 1 are represented by the same symbols, and a detailed description to such elements will be omitted.

The light source apparatus 20 is provided with an LD 1-1, and adjusts the effective heat generation amount $Q_{eff}$ of LD 1-1. That is, the light source apparatus 20 can change the effective light power $P_{eff}$ of LD 1-1 within the adjustable range of the effective heat generation amount $Q_{eff}$ as represented by equation (8), while not changing the effective light power $P_{eff}$ of LD 1-1. Accordingly, the temperature stability can be ensured without separately providing a temperature adjuster such as a Peltier device for stable operation, similar to the first embodiment.

Third Embodiment

Figure 8:
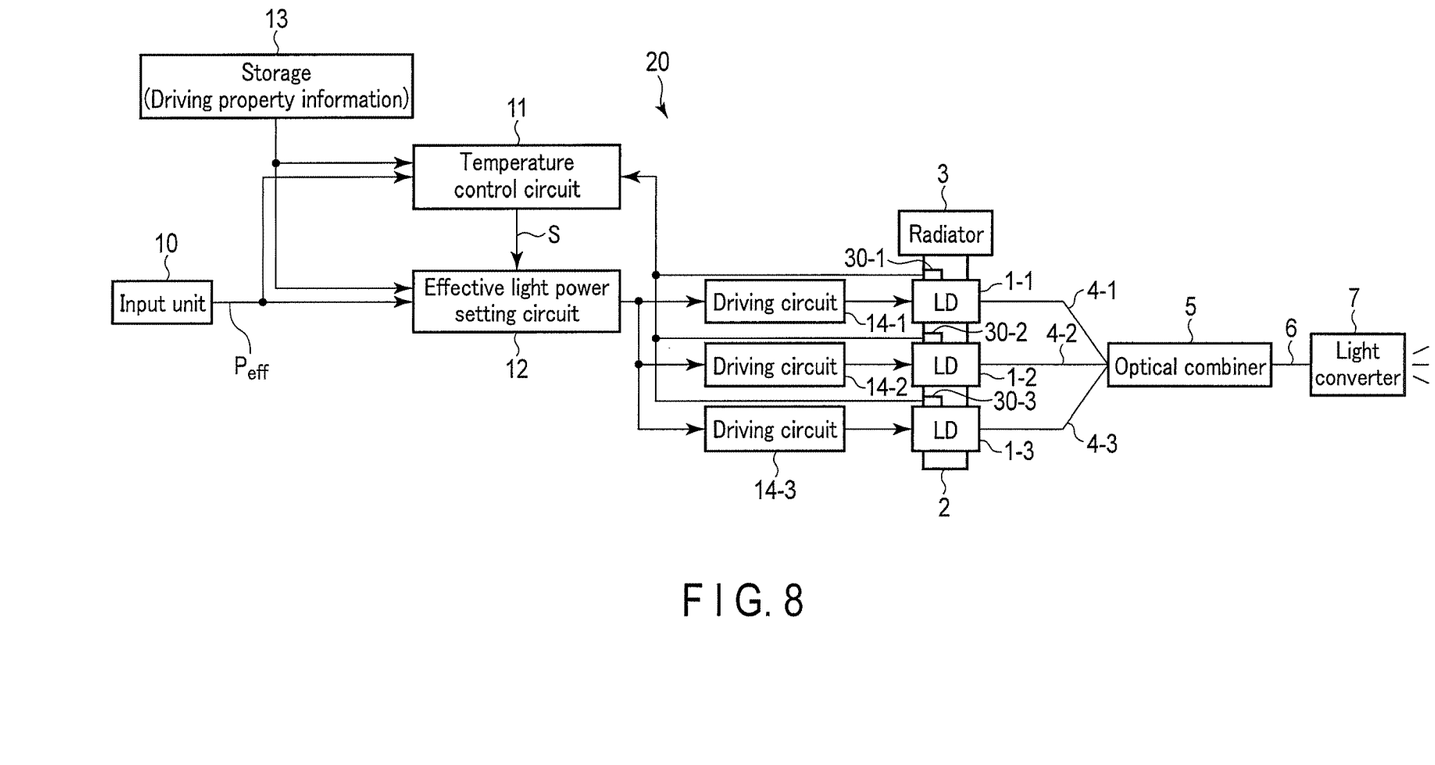
FIG. 8 is a block diagram illustrating a third embodiment of the light source apparatus according to the present invention.

FIG. 8 illustrates a configuration of the light source apparatus 20 according to a third embodiment. The same elements as those shown in FIG. 1 are represented by the same symbols, and a detailed description to such elements will be omitted.

Figure 9:
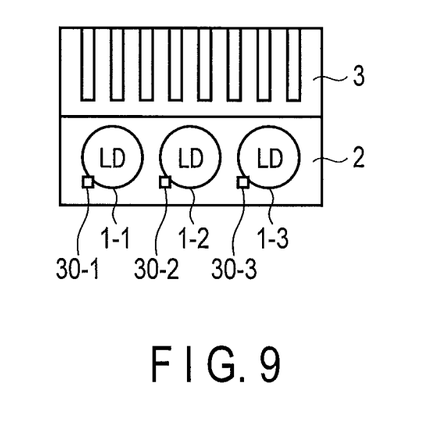
FIG. 9 illustrates an arrangement of temperature sensors.

The light source apparatus 20 is provided with temperature sensors 30-1 to 30-3, which act as a temperature detector, in the vicinity of each LD 1-1 to LD 1-3. FIG. 9 illustrates the arrangement of temperature sensors 30-1 to 30-3. Each of the temperature sensors 30-1 to 30-3 is provided on the mount 2 to be in contact with each LD 30-1 to LD 30-3. The temperature sensor 30-1 detects the temperature of LD 1-1 and outputs an electrical signal indicative of the detected temperature. The temperature sensor 30-2 detects the temperature of LD 1-2 and outputs an electrical signal indicative of the detected temperature. The temperature sensor 30-3 detects the temperature of LD 1-3 and outputs an electrical signal indicative of the detected temperature. The temperature sensors 30-1 to 30-3 may be any general temperature sensors such as a thermistor, a thermocouple or a sensor measuring a temperature without contact. The electrical signal output from each of the temperature sensors 30-1 to 30-3 is sent to the temperature control circuit 11.

The temperature control circuit 11 receives the electrical signal output from each of the temperature sensors 30-1 to 30-3, and adjusts the peak current value of the cyclic pulse waveform or the duty cycle set as the driving condition S of each of LD 1-1 to LD 1-3 so that the temperature of each of LD 1-1 to LD 1-3 becomes a predetermined temperature condition based on the electrical signal (the temperature of each of LD 1-1 to LD 1-3). The predetermined temperature condition is a condition where the temperature of each of LD 1-1 to LD 1-3 detected by respective temperature sensors 30-1 to 30-3 becomes a predetermined temperature.

According to the third embodiment, the peak current value of the cyclic pulse waveform or the duty cycle set as the driving condition S is adjusted so that the temperature of each of LD 1-1 to LD 1-3 becomes the predetermined temperature condition based on the temperature of each of LD 1-1 to LD 1-3 output from the respective temperature sensors 30-1 to 30-3. This realizes the similar advantages to the first embodiment.

Fourth Embodiment

Figure 10:
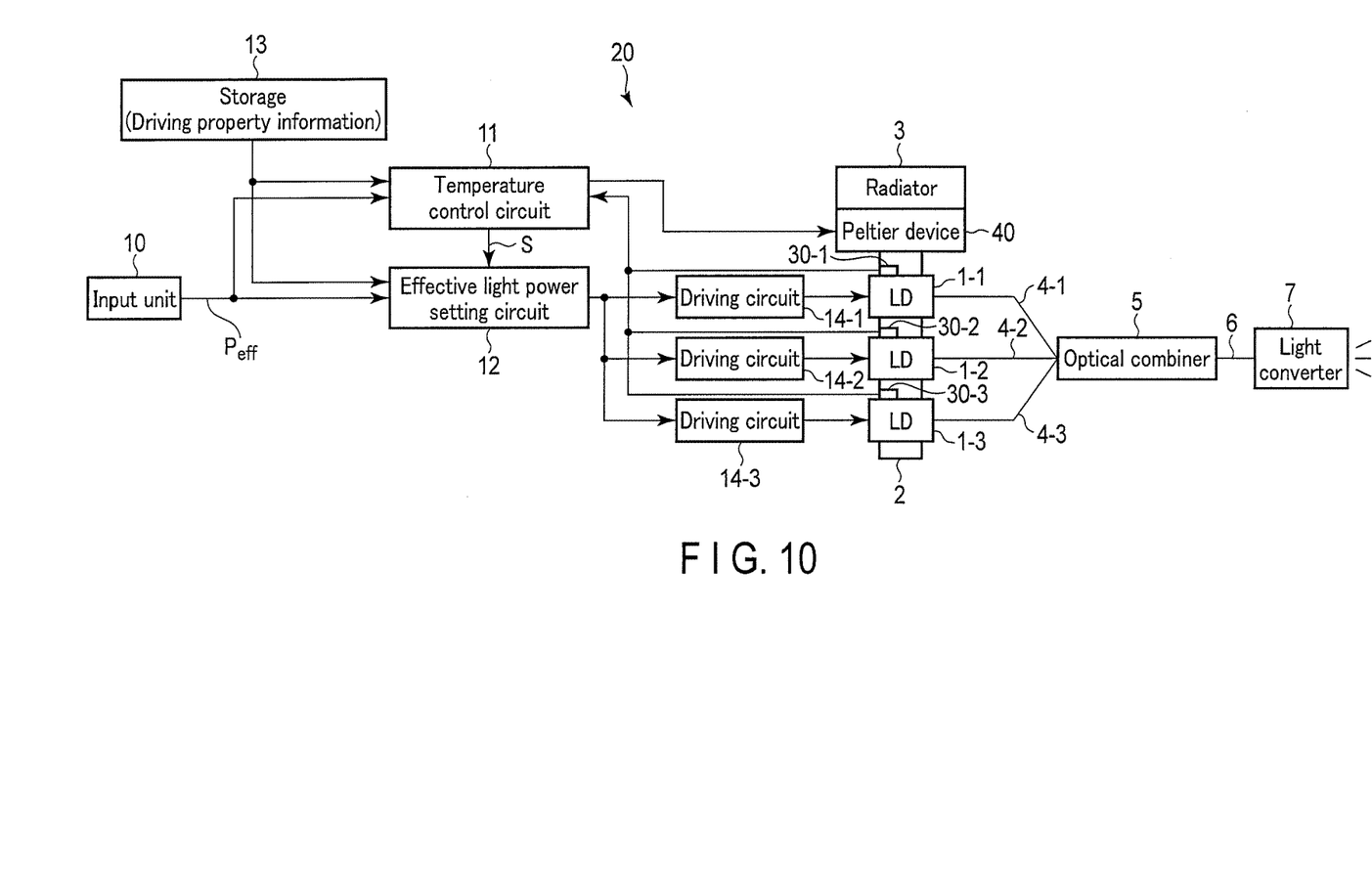
FIG. 10 is a block diagram illustrating a fourth embodiment of the light source apparatus according to the present invention.

FIG. 10 illustrates a configuration of the light source apparatus 20 according to a fourth embodiment. The same elements as those shown in FIG. 8 are represented by the same symbols, and a detailed description to such elements will be omitted.

The light source apparatus 20 is provided with temperature sensors 30-1 to 30-3 which act as a temperature detector in the vicinity of respective LD 1-1 to LD 1-3, in the manner similar to the third embodiment.

Figure 11:
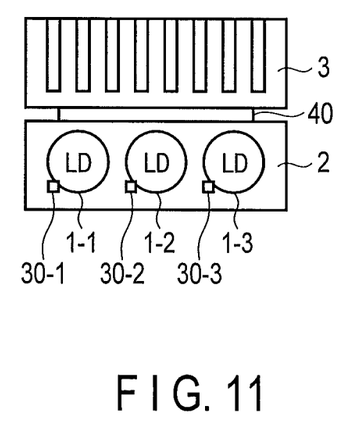
FIG. 11 illustrates the configuration of the peripheral portion of LDs.

The mount 2 is provided with the radiator 3 through a Peltier device 40 acting as a temperature adjuster. FIG. 11 illustrates the arrangement of the Peltier device 40. The Peltier device 40 is provided between the mount 2 and the radiator 3. The Peltier device 40 adjusts the temperatures of LD 1-1 to LD 1-3 when cooling or heating. For example, one Peltier device 40 is provided. The number of the Peltier devices 40 is smaller than the number of LDs (three LD 1-1 to LD 1-3 in this case).

The temperature control circuit 11 obtains the temperature of each of LD 1-1 to LD 1-3 from the electrical signals output from the respective temperature sensors 30-1 to 30-3, drives the Peltier device 40 so that the temperature detected by the respective temperature sensors 30-1 to 30-3 becomes a predetermined temperature, and cools or heats each of LD 1-1 to LD 1-3.

In this embodiment, LD 1-1 to LD 1-3 are different in type and properties. The driving property information of each of LD 1-1 to LD 1-3 is stored individually in the storage 13. LD 1-1 to LD 1-3 are arranged so that the heat conductance between the Peltier device 40 and each of LD 1-1 to LD 1-3 becomes equal.

The temperature control circuit 11 controls the temperature of the Peltier device 40 based on the temperature detected by one of the temperature sensors 30-1 to 30-3 which is provided in the vicinity of one of LD 1-1 to LD 1-3 having the highest heat generation amount, the highest required effective output, or the highest temperature.

Specifically, the temperature control circuit 11 compares a predetermined temperature with the temperature detected by one of the temperature sensors 30-1 to 30-3 provided in the vicinity of respective LD 1-1 to LD 1-3. As a result of comparison, if the detected temperature is higher than the predetermined temperature, the temperature control circuit 11 reduces a current value to be applied to the Peltier device 40. If the detected temperature is lower than the predetermined temperature, the temperature control circuit 11 increases a current value to be applied to the Peltier device 40.

The temperature control circuit 11 may determine the current value by the PID control theory.

According to the fourth embodiment, the temperature detected by the temperature sensors 30-1 to 30-3 provided in the vicinity of respective LD 1-1 to LD 1-3 is compared with the predetermined temperature, and the temperature of the Peltier device 40 is controlled based on the comparison results. Thus, even if the output of each of LD 1-1 to LD 1-3 is set to be different, the heat generation amount Q of each of LD 1-1 to LD 1-3 can be equalized, thereby controlling the temperatures of LD 1-1 to LD 1-3 to be equal with each other and enhancing output stability even with a Peltier device 40 acting as a temperature adjuster.

The forward voltage $V_f$ of each of LD 1-1 to LD 1-3 may vary in accordance with the driving current. In this case, table data of the forward voltages $V_f$ and the driving currents may preferably be stored as the driving property information for each of LD 1-1 to LD 1-3 in the storage 13. The configuration is optimal if the efficiency is maximum and the peak current is rated.

On the other hand, if the forward voltage $V_f$ of each of LD 1-1 to LD 1-3 does not vary in accordance with the driving current, the temperature control circuit 11 may set one of the driving current pulses $PI_1$ to $PI_3$ ($I_{drv}$) having the greatest efficiency, not a current with which the light output becomes the maximum rated value $P_{max}$, as a peak current, when obtaining the duty cycle D for one of LD 1-1 to LD 1-3 having the greatest heat generation amount Q.

If the current with which the greatest efficiency is realized is not sufficient (when the duty cycle D exceeds 100%), the minimum current with which the duty cycle D is 100% or less is set as the peak current.

Embodiment of Endoscope Apparatus

An embodiment of an endoscope apparatus of the present invention will be described with reference to the drawings. The same elements as those shown in FIG. 10 are represented by the same symbols, and a detailed description to such elements will be omitted.

Figure 12:
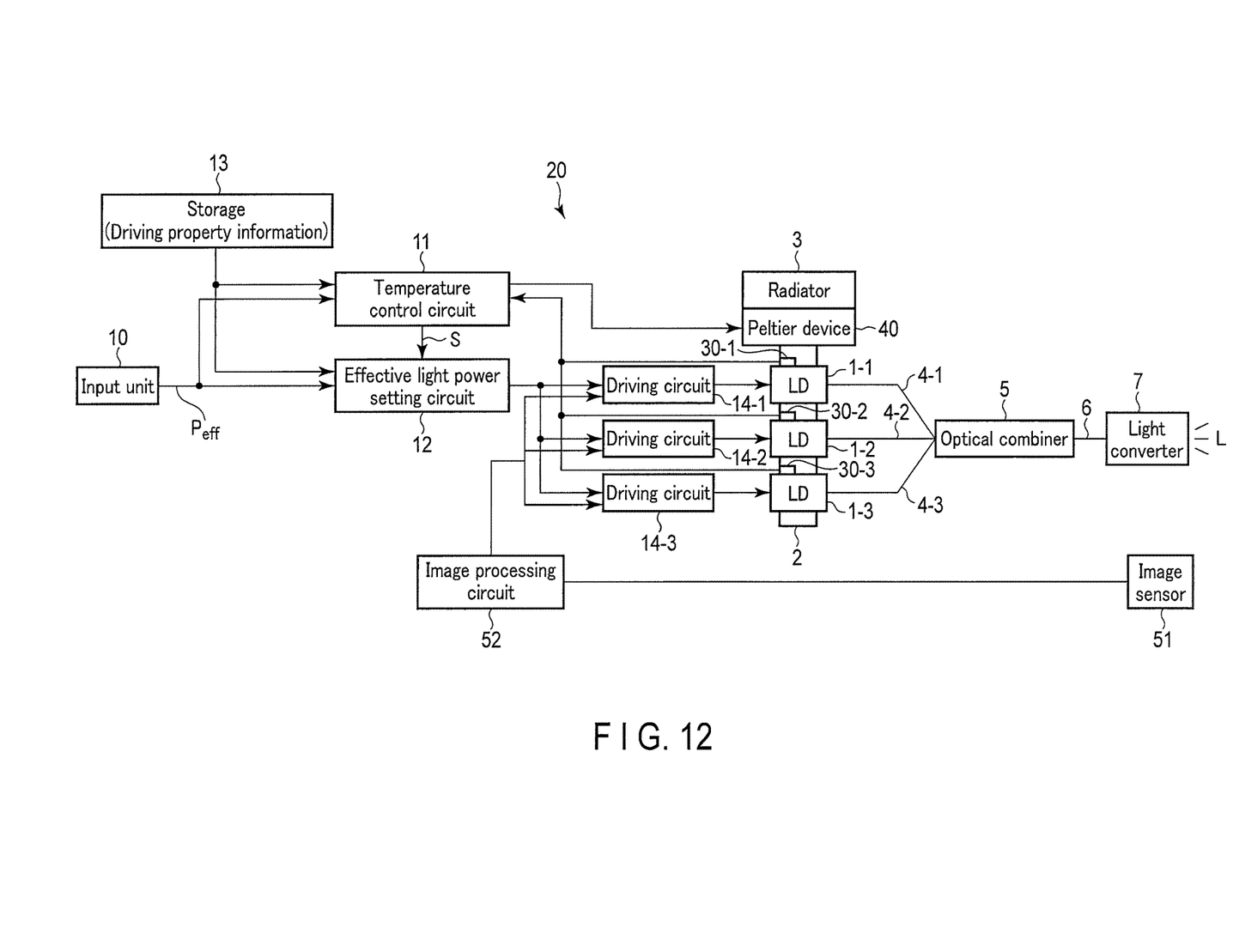
FIG. 12 is a block diagram illustrating an embodiment of an endoscope apparatus according to the present invention.

FIG. 12 is a block diagram illustrating the entire configuration of an endoscope apparatus 50 including the light source apparatus 20. An image sensor 51 is provided at a distal end of an endoscope insertion portion. The endoscope insertion portion may be inserted into the subject's body to image inside of the subject's body and acquire an image, or to perform treatment to the inside of the subject's body. The image sensor 51 images the inside of the subject's body and outputs an image signal when inserted into the subject's body. The image signal output from the image sensor 51 is transmitted to an image processing circuit 52.

The image processing circuit 52 receives the image signal output from the image sensor 51, and performs image processing to the image signal to obtain an image of the inside of the subject's body. The image processing circuit 52 generates a synchronization signal, and transmits the synchronization signal to the image sensor 51. The image sensor 51 synchronizes with the synchronization signal from the image processing circuit 52, and performs an imaging operation (exposure operation).

In addition, the image processing circuit 52 transmits the synchronization signal to each of the driving circuits 14-1 to 14-3. Each of the driving circuits 14-1 to 14-3 drives each of LD 1-1 to LD 1-3 by applying the driving waveform to allow LD 1-1 to LD 1-3 to emit laser light. Each of the driving circuits 14-1 to 14-3 adjusts a rising timing of the driving current pulses $PI_1$ to $PI_3$ to be applied to each of LD 1-1 to LD 1-3, in accordance with the synchronization signal from the image processing circuit 52.

Figure 13:
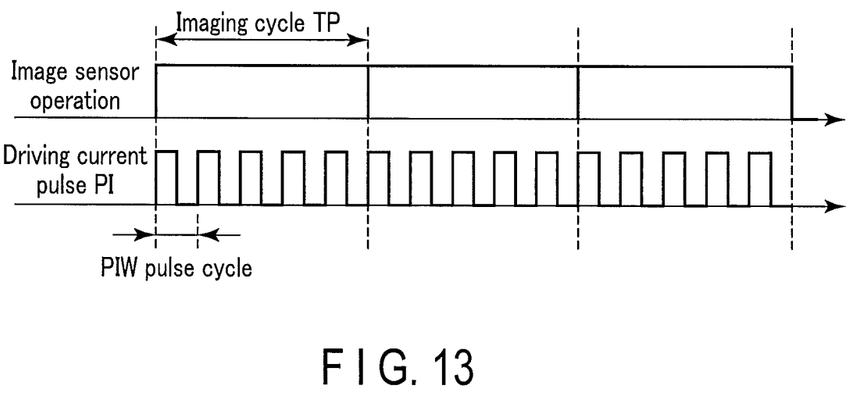
FIG. 13 illustrates operating timings of an image sensor and LDs.

FIG. 13 illustrates the operation timings of the image sensor 51 and LD 1-1 to LD 1-3. The image sensor 51 performs an imaging operation (exposure operation) for each imaging cycle TP to acquire an image frame. The driving current pulses $PI_1$ to $PI_3$ applied to respective LD 1-1 to LD 1-3 repeat a high level and low level with the pulse cycle PIW. The pulse cycle PIW corresponds to the cycle $(T_1+T_2)$ shown in FIG. 3.

Accordingly, each of the driving circuits 14-1 to 14-3 sets the pulse cycle PIW of each of the driving current pulses $PI_1$ to $PI_3$ to be respectively applied to LD 1-1 to LD 1-3 to be a fraction of a natural number of the image cycle (cycle to acquire an image frame) TP of the image sensor 51.

According to the embodiment of the endoscope apparatus, the rising timing of the driving current pulses $PI_1$ to $PI_3$ to be applied to each of LD 1-1 to LD 1-3 in accordance with the synchronization signal to allow the image sensor 51 to perform an imaging operation (exposure operation) is adjusted; for example, the pulse cycle PIW of each of the driving current pulses $PI_1$ to $PI_3$ is set to be a fraction of a natural number of the image cycle TP of the image sensor 51. Accordingly imaging information without variation can be obtained.

This embodiment is not limited to using the pulse width modulation (PWM) that varies the duty cycle of the pulse waveform, but may change the cycle while setting the pulse widths of the driving current pulses $PI_1$ to $PI_3$ to be a fixed value. In this case, the pulse width of each of the driving current pulses $PI_1$ to $PI_3$ needs to be sufficiently short in comparison with the image frame cycle of the image sensor 51.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A light source apparatus comprising:
    a plurality of light-emitters configured to emit light;
    a driving circuit configured to apply a driving waveform to the plurality of light-emitters;
    a temperature control circuit configured to:
        receive, as an input, a predetermined effective light power of the light emitted from the plurality of light-emitters; and
        control the plurality of light-emitters to be in a predetermined heat generation state by increasing or decreasing a heat generation amount of the plurality of light-emitters without changing the predetermined effective light power of the light emitted from the plurality of light-emitters by adjusting a driving condition of the plurality of light-emitters;
    an effective light power setting circuit configured to drive the driving circuit to allow the plurality of light-emitters to emit light with the predetermined effective light power, in accordance with the driving condition adjusted by the temperature control circuit;
    at least one temperature detector configured to detect a temperature of the plurality of light-emitters,
        wherein the predetermined heat generation state is a state where the temperature of the plurality of light-emitters detected by the at least one temperature detector is a predetermined temperature, and
        wherein the temperature control circuit is configured to adjust the driving condition so that the temperature of the plurality of light-emitters detected by the temperature detector becomes the predetermined temperature; and
    at least one temperature adjuster configured to adjust a temperature of the plurality of light-emitters,
    wherein a number of the at least one temperature adjuster is smaller than a number of the plurality of light-emitters,
    wherein the at least one temperature detector is provided adjacently to a first light-emitter of the plurality of light-emitters, and
    wherein the temperature control circuit is configured to drive the at least one temperature adjuster so that the first light-emitter becomes the predetermined temperature, based on the temperature of the first light-emitter detected by the at least one temperature detector.

2. The light source apparatus according to claim 1, wherein the plurality of the light-emitters are arranged so that a heat conductance between each of the plurality of the light-emitters and the temperature adjuster is equal.

3. A light source apparatus comprising:
    at least one light-emitter configured to emit light;
    a driving circuit configured to apply a driving waveform to the at least one light-emitter, wherein the driving waveform includes a cyclic pulse waveform;
    a temperature control circuit configured to:
        receive, as an input, a predetermined effective light power of the light emitted from the at least one light-emitter; and
        control the at least one light-emitter to be in a predetermined heat generation state by increasing or decreasing a heat generation amount of the at least one light-emitter without changing the predetermined effective light power of the light emitted from the at least one light-emitter by adjusting a driving condition of the at least one light-emitter; and
    an effective light power setting circuit configured to drive the driving circuit to allow the at least one light-emitter to emit light with the predetermined effective light power, in accordance with the driving condition adjusted by the temperature control circuit,
    wherein one of a peak current value of the cyclic pulse waveform and a duty cycle is set as the driving condition,
    wherein the effective light power setting circuit is configured to determine the other of the peak current value of the cyclic pulse waveform and the duty cycle, which has not been set as the driving condition, so that an effective light power of the light emitted by the at least one light-emitter becomes the predetermined effective light power, and
    wherein a cycle of the cyclic pulse waveform is a cycle where the at least one light-emitter is not thermally responsive.

4. An endoscope apparatus comprising:
    at least one light-emitter configured to emit light;
    a driving circuit configured to apply a driving waveform to the at least one light-emitter, wherein the driving waveform includes a cyclic pulse waveform;
    a temperature control circuit configured to:
        receive, as an input, a predetermined effective light power of the light emitted from the at least one light-emitter; and
        control the at least one light-emitter to be in a predetermined heat generation state by increasing or decreasing a heat generation amount of the at least one light-emitter without changing the predetermined effective light power of the light emitted from the at least one light-emitter by adjusting a driving condition of the at least one light-emitter;
    an effective light power setting circuit configured to drive the driving circuit to allow the at least one light-emitter to emit light with the predetermined effective light power, in accordance with the driving condition adjusted by the temperature control circuit,
    wherein one of a peak current value of the cyclic pulse waveform and a duty cycle is set as the driving condition, and
    wherein the effective light power setting circuit is configured to determine the other of the peak current value of the cyclic pulse waveform and the duty cycle, which has not been set as the driving condition, so that an effective light power of the light emitted by the at least one light-emitter becomes the predetermined effective light power; and an imaging apparatus, wherein a cycle of the cyclic pulse waveform is set to be a fraction of a natural number of an image frame cycle of the imaging apparatus.

* * * * *